United States Patent
Fry

(10) Patent No.: US 6,423,322 B1
(45) Date of Patent: Jul. 23, 2002

(54) ORGANOPOLYSILOXANE GELS FOR USE IN COSMETICS

(75) Inventor: Bryan E. Fry, Tecumseh, MI (US)

(73) Assignee: Wacker Silicones Corporation, Adrian, MI (US)

( * ) Notice: Subject to any disclaimer, the term of this patent is extended or adjusted under 35 U.S.C. 154(b) by 0 days.

(21) Appl. No.: 09/317,093

(22) Filed: May 22, 1999

(51) Int. Cl.$^7$ ................................................. A61K 6/00
(52) U.S. Cl. ...................................................... 424/401
(58) Field of Search ................................ 424/400, 401, 424/59, 60, 64, 43, 47, 46; 514/772

(56) References Cited

U.S. PATENT DOCUMENTS

| | | |
|---|---|---|
| 3,159,601 A | 12/1964 | Ashby |
| 3,159,662 A | 12/1964 | Ashby |
| 3,220,972 A | 11/1965 | Lamoreaux |
| 3,715,334 A | 2/1973 | Karstedt |
| 3,775,452 A | 11/1973 | Karstedt |
| 3,814,730 A | 6/1974 | Karstedt |
| 4,594,134 A | 6/1986 | Hanada et al. |
| 4,742,142 A | 5/1988 | Shimizu et al. |
| 4,806,430 A | 2/1989 | Spielvogel et al. |
| 4,970,252 A | 11/1990 | Sakuta et al. |
| 4,980,167 A | 12/1990 | Harashima et al. |
| 4,987,169 A | 1/1991 | Kuwata et al. |
| 5,136,068 A | 8/1992 | Bahr et al. |
| 5,236,986 A | 8/1993 | Sakuta |
| 5,266,321 A | 11/1993 | Shoukuzaki et al. |
| 5,412,004 A | 5/1995 | Tachibana et al. |
| 5,599,533 A | 2/1997 | Stepniewski |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,849,314 A | 12/1998 | Dobkowski et al. |
| 5,854,336 A | 12/1998 | Divone, Sr. et al. |
| 5,859,069 A | 1/1999 | Yanagida |

FOREIGN PATENT DOCUMENTS

| | | |
|---|---|---|
| EP | 0 184 598 A1 | 6/1986 |
| EP | 0 790 055 A1 | 1/1997 |
| EP | 0 827 983 A2 | 3/1998 |
| WO | WO 97/44010 | 11/1997 |
| WO | WO 98/00102 | 1/1998 |
| WO | WO 98/00103 | 1/1998 |
| WO | WO 98/00104 | 1/1998 |
| WO | WO 98/00105 | 1/1998 |
| WO | WO 98/18438 | 5/1998 |

OTHER PUBLICATIONS

Japanese Abstract Patent No. JP 1190757, Published Jul. 31, 1989, Inventor Shimizu Toru.
Japanese Abstract Patent No. JP 2172906, Published Jul. 4, 1990, Inventor Imamura Akihiro.
Japanese Abstract Patent No. JP 3197413, Published Aug. 28, 1991, Inventor Yamazoe Yoshinori.
Japanese Abstract Patent No. JP 1207354, Published Aug. 21, 1989, Inventor Shimizu Toru.
Japanese Abstract Patent No. JP 61194009, Published Aug. 28, 1996, Inventor Harashima Asao.
Japanese Abstract Patent No. JP 1250305, Published Oct. 5, 1989, Inventor Shukuzaki Koichi.

*Primary Examiner*—Dameron Jones
(74) *Attorney, Agent, or Firm*—Brooks & Kushman P.C.

(57) ABSTRACT

Soft, creamy translucent and transparent gels suitable for use in cosmetic applications may be prepared by hydrosilylating an unsaturated MQ resin or its equivalent with an Si—H functional organopolysiloxane cross-linker having Si—H functionality along its polysiloxane backbone, in the presence of a low viscosity and preferably volatile organopolysiloxanes. The stable gels obtained may be converted to creamy gels of a wide range of consistency by simple shearing. Gel firmness can be maintained through addition of a catalyst inhibitor to the gel formulation.

21 Claims, No Drawings

ORGANOPOLYSILOXANE GELS FOR USE IN COSMETICS

TECHNICAL FIELD

The present invention pertains to organopolysiloxane gels suitable for use in cosmetic applications.

BACKGROUND ART

Oganopolysiloxanes have been used in numerous cosmetic applications for many years. In some of these applications, for example, organopolysiloxanes such as silicone fluids have been employed either in their native form as oils for carriers for other cosmetic ingredients, or in the form of a variety of emulsions. In many of the latter cases, a surfactant is necessary in order to keep the silicone fluid in stable suspension or dispersion. Somewhat more recently, numerous cosmetic formulations have employed creams or pastes which include organopolysiloxane gels.

U.S. Pat. No. 5,654,362 discloses silicone gels prepared by reacting a linear, Si—H functional polysiloxane with an $\alpha,\omega$-diene, for example 1,5-hexadiene, in the presence of a platinum hydrosilylation catalyst and a low molecular weight silicone oil. The reaction is continued until a gel is formed following which the silicone gel may be crumbled into a powder and used to thicken solvents, or by addition of further silicone oil, to form a silicone paste. The products are employed to thicken solvents such as silicone oils to a gel-like consistency. A variety of cosmetic products such as an anti-perspirants, deodorants, skin creams, etc., are disclosed. The use of highly flammable diene hydrocarbons in the preparation is a disadvantage. Moreover, creams formed from solid powders are said not to provide acceptable properties, as indicated by U.S. Pat. No. 4,980,167, wherein such formulations are said to suffer from lack of lubricity.

U.S. Pat. No. 5,859,069 discloses a gelatinous external skin treatment composition prepared from an organopolysiloxane elastomer powder having spherical particles with an average particle size of 1.0 to 15.0 μm, a silicone oil, and a polyether-modified silicone. The '069 patent indicates that prior formulations employing silicone resins are unsuitable for such uses, as they leave a filmy feeling on the skin. The polyether-modified silicone is disclosed as being absolutely necessary; and if amounts of less than 1.0% by weight are used, gelation becomes insufficient and the composition becomes unsuitable for use in cosmetics. Gelatinous external skin treatment compositions containing the spherical powder, 5–75% by weight of silicone oil, and 1–20% by weight of polyether-modified silicone are disclosed. Preparation of spherical elastomer particles is not straightforward. Moreover, the requirement for a polyether-modified silicone increases cost.

U.S. Pat. No. 5,811,487 like the '362 patent previously disclosed, describes low molecular weight siloxane fluids thickened with silicone elastomers prepared by reaction of Si—H functional siloxanes and an $\alpha,\omega$-unsaturated hydrocarbon. However in the '487 patent, the Si—H siloxane is first partially reacted with a monoalkenyl functionalized polyether to provide polyether functionality. The polyether-functionalized organopolysiloxane is stated to be necessary by to prepare compositions containing dispersed water, consistent with the teachings of U.S. Pat. No. 5,859,069 discussed above.

U.S. Pat. No. 5,760,116 discloses a composition containing the hydrosilylation addition product of a linear alkenyl-functionalized polyorganosiloxane and an Si—H functional MQ resin. Monovinyl-functional linear polyorganosiloxanes are included in exemplified formulations as alkenyl-functionalized polyorganosiloxanes in addition to divinyl-functional polyorganosiloxanes. Uniform liquid compositions formed by first preparing a gel from these ingredients, and then dispersing the gel in a further silicone having a viscosity below 1000 centistokes is disclosed. Cosmetic compositions containing these silicone compositions are also disclosed.

U.S. Pat. No. 5,854,336 discloses a process for preparing cosmetic products which involves feeding a silicone elastomer composition consisting of a silicone rubber and a carrier fluid into a reactor, mixing the composition in the reactor, delivering the composition from the reactor to a high pressure pump, and from there into a device for reducing the particles of rubber into smaller sizes. The device for reducing particle size is preferably a high pressure feed homogenizer, most preferably a sonolator. Use of high pressure pumps and devices such as sonolators increase the expense of the product.

EP 0790 055 A1 discloses compositions containing a partially reticulated elastomeric organopolysiloxane and a fatty component such as a triglyceride for use in skin care or make-up formulas. What is meant by "partially reticulated" is not defined in the specification, which refers to U.S. Pat. No. 5,266,321 for its description of suitable organopolysiloxanes.

Examples of cosmetic formulations employing silicone gels are also disclosed in International PCT Applications WO97/44010; WO98/18438; WO98/00105; WO98/00104; WO98/00103; WO98/00102, and like patents. It can be clearly seen from such patents that the range of formulations includes antiperspirants, both liquid and solid, facial creams, moisturizers, and other products. It should also be apparent from a review of these references that there are considerable differences between the variety of organosilicone gels. In particular, some of these gels provide an unacceptable oily feeling when such is not desired. Other gels are more difficult to produce, and unnecessarily increase the cost of formulation. It would be desirable to be able to produce gels in a simple fashion from well-recognized and essentially non-toxic ingredients, to produce a product which avoids the stringiness of other gels, and which can be emulsified without the use of extremely high pressure devices such as sonolators and the like.

SUMMARY OF THE INVENTION

It has now been unexpectedly discovered that organopolysiloxane gels containing a low viscosity and preferably volatile silicone oil may be easily prepared by the hydrosilylation reaction of a vinyl functional MQ resin with an Si—H functional poly(methylhydrogen)dimethylsiloxane in the presence of the low viscosity fluid and a small amount of platinum hydrosilylation catalyst. It has also been discovered that addition of relatively small amounts of hydrosilylation catalyst poisons such as organosulphur compounds, particularly mercaptoalkyl organopolysiloxanes, produces compositions which retain their stability over longer periods of time than when the organosulphur compounds are not employed. The resulting gels are non-stringy gels which may be easily homogenized to form a stable cream or paste without the use of high pressure or other complex mixing arrangements.

DESCRIPTION OF THE PREFERRED EMBODIMENTS

The organopolysiloxane gels of the subject invention contain a low viscosity and preferably volatile silicone oil, intimately associated with a gel matrix produced by the cross-linking of a vinyl functional MQ resin with an Si—H functional organopolysiloxane which contains Si—H functionality distributed along its backbone rather than at the termini.

The low viscosity and preferably volatile organopolysiloxane may be a low molecular weight oligomeric polydialkylsiloxane, or a cyclic siloxane. Most preferably, the low viscosity organopolysiloxane is an oligomeric polydimethylsiloxane or a cyclic polydimethylsiloxane. Other alkyl, aryl, alkaryl, and aralkyl groups are also acceptable, of course, for example, phenyl groups, benzyl groups, $C_1$–$C_{18}$ alkyl groups, and the like. However, because of cost considerations and the ease of formulation, organopolysiloxanes with methyl groups attached to the silicon atoms are highly preferred. Most preferably, the organopolysiloxanes are linear trimethylsilyl terminated polydimethylsiloxanes having on average from 2 to 50 silicon atoms in the organopolysiloxane backbone inclusive of the trimethylsilyl end groups. If volatility is desired, the number of silicon atoms should be greatly restricted, for example, to below 10, and preferably below 6. However, if relatively low viscosity but non-volatile fluids can be tolerated, extensions of the organopolysiloxane backbone to higher numbers of silicon atoms, for example, to 50 or 500 silicon atoms is possible. These non-volatile fluids should have viscosities greater than about 10 cSt, and up to about 2000 cSt. The organopolysiloxanes may also be slightly cross-linked, as long as the cross-linking does not overly increase the viscosity. Viscosity is preferably below 100 cSt, 100 cSt, more preferably below 10 cSt, and most preferably, in the case of volatile organopolysiloxanes, less than 5 cSt.

Preferably, the organopolysiloxanes are volatile organopolysiloxanes. As indicated previously, volatility can be achieved in linear organopolysiloxanes by selection of oligomeric organopolysiloxanes with at most about 6 to 10 silicon atoms in the organopolysiloxane backbone. Preferably, however, cyclic organopolysiloxanes having from 3 to 6 silicon atoms are utilized, for example, hexamethylcyclotrisiloxane, octamethylcyclotetrasiloxane, decamethylcyclopentasiloxane, dodecamethylcyclohexasiloxane, and the like. As with the linear organopolysiloxanes, groups other than methyl groups may be present, for example, $C_1$–$C_{18}$ alkyl groups, preferably $C_{1-4}$ alkyl groups, aryl groups, and the like. In addition, and also as is the case for the linear polysiloxanes, functional groups which do not interfere with the stability of the organopolysiloxane gels or with the ability to use these in cosmetic formulations may be tolerated. In particular, examples include hydroxyl (silanol) groups, alkoxy groups, for example, those which are relatively hydrolytically stable, and the like. Compounds containing reactive groups such as acetoxy groups, methoxy groups, ethoxy groups and the like, should generally be avoided unless they are retained for some special purpose in the cosmetic formulations. It is not desired to include any halo-functional compounds in the organopolysiloxane gels. Please note in this respect that minor amounts of such groups are generally unavoidable in organosiloxane resins due to their method of preparation.

A necessary component of the organopolysiloxane gel is a vinyl functional MQ resin or similar, highly crosslinked resin containing M, D, Q, and/or T moieties. Such resins are by now well-known in the art. In the organopolysiloxane art, the term "resin" is not applied to polymers in general, but is restricted for the use in describing relatively highly cross-linked and often relatively high molecular weight products produced by the reaction of silanes which are capable of forming three-dimensional networks. The term M refers to monofunctional units while the term Q refers to tetrafunctional units. In other words, an MQ resin contains predominantly M units wherein silicon is attached to only one oxygen in the cross-linked molecules, and $SiO_{4/2}$ Q units wherein each silicon atom is attached to four other oxygen atoms, resulting in a high level of cross-linking. In many MQ resins, small amounts of difunctional $R_2SiO_{2/2}$ and trifunctional $RSiO_{3/2}$ (D and T units, respectfully), are also present. MQ resins are frequently produced by the hydrolysis of silanes such as tetraethoxysilane, vinyldimethylethoxysilane and trimethylethoxysilane. The resulting MQ resin frequently retains some residual alkoxy functionality as a result of the method of its preparation, and will occasionally include other functionalities such as silanol functionality as well. A preferred MQ resin is MQ resin 804, available from Wacker Silicones Corporation, Adrian, Mich., which contains approximately 1.8 weight percent vinyl functionality. MQ resins having unsaturation other than vinyl, including vinyloxy, allyl, allyloxy, propenyl, etc., are less commonly available, but may be used also. The various unsaturated resins may be used alone or in admixture with other unsaturated resins.

The Si—H functional organopolysiloxane cross-linking agent is a necessary part of the present gel formulation. Applicants have unexpectedly discovered that when Si—H-terminated organopolysiloxanes are used as crosslinkers, these gels tend to have a stringy appearance. Rather, the crosslinker must be an Si—H functional organopolysiloxane which contains at least some Si—H functional units along its polymer backbone. It may or may not in addition to these Si—H functional units, also include terminal Si—H units. A preferred crosslinker is EL Crosslinker 525, a poly(methylhydrogen)dimethylsiloxane containing approximately 0.54 weight percent silicon-bonded hydrogen atoms.

The ratio of moles of unsaturation in the MQ resin to moles of Si—H is preferably in the range of 0.2 to 1.5, more preferably 0.3 to 1.2, and most preferably 0.4 to 0.9. Ratios of 0.85 to 0.88 have proven quite satisfactory.

A hydrosilylation catalyst is also required. Suitable hydrosilylation catalysts are well-known, and widely available from numerous sources. Preferred hydrosilylation catalysts are platinum compounds such as those disclosed in U.S. Pat. Nos. 3,159,601; 3,159,662; 3,220,972; 3,715,334; 3,775,452; and 3,814,730, and Germany published application DE 195 36176 A1, supplied in a solvent suitable for use in cosmetic formulations, such as propanediol. Other solvents may be used as well, provided that they are cosmetically acceptable, or can be removed from the gel, for example, by exposure to low pressures or stripping. The amounts of low viscosity silicone, MQ resin, and crosslinker are not critical, however, these must be present in such quantities that a stable gel is obtainable which will not separate upon standing. If too little MQ resin or too little crosslinker is used, the composition will frequently remain liquid instead of gelling. If too much crosslinker or MQ resin is obtained, a solid or crumbly gel or product will be obtained. The actual amounts can be determined by simple experimentation. Preferred compositions contain from about 60% to about 90% low viscosity organopolysiloxane, from about 5% to about 25% MQ resin, and from about 1% to about 8% Si—H functional crosslinker. More preferably, the compositions contain from 60 to 85% by weight volatile organopolysiloxane, 10 to 20% MQ resin, and 1 to 5% crosslinker. These percentages are percentages by weight based on the total weight of the gel.

The preparation of the gel is readily accomplished. In general, all of the ingredients except the catalyst are added and stirred slowly until a homogenous mixture is obtained, following which the catalyst is added with continual stirring. The composition can be left at room temperature until a gel is formed, or can be heated. Preferably, the composition is heated to a temperature between 70° C. and 130° C., more preferably between 90° C. and 110° C. until the mixture solidifies or gels. Gelation typically takes place within two to five hours, preferably within a maximum of about three hours, and typically within about 45 minutes. The gel is then homogenized to a smooth consistency using standard high shear mixing techniques such as the use of an Ultra-Turax™ mixer or the like. High pressure mixing and recirculated mixing techniques are not necessary.

Following homogenization of the gel to a creamy consistency, numerous cosmetic ingredients can be added, such as glycerin, perfumes, emollients, lanolin, oils, pigments, U.V. absorbers, dyes, etc. Thickeners such as pyrogenic silica and other ingredients may also be added at this point to increase the viscosity of the cream to form paste-like products.

The number and type of cosmetic ingredients which may be added is not overly critical, and can be easily selected by one skilled in the art. In the application herein the term "cosmetically acceptable ingredients" includes all ingredients which can be added by a cosmetic formulator which are cosmetically acceptable for use on the skin. Many such ingredients are listed in standard references, for example INTERNATIONAL COSMETIC INGREDIENT DICTIONARY AND HANDBOOK, ©1997, Cosmetic, Toiletry and Fragrance Assoc., Washington, D.C.

The creamy gels of the subject invention may be used in all cosmetic formulations where silicone emulsions and other products have been used in the past, including, without limitation, skin care products such as antiperspirants, deodorants, sun care, after sun care, moisturizers, creams and lotions; color cosmetic products, such as facial powder, eye powder, eye shadow, liquid foundation, liquid-to-powder foundations, and lipsticks; and hair care products such as hair conditioners, volume enhancers, and the like.

Having generally described this invention, a further understanding can be obtained by reference to certain specific examples which are provided herein for purposes of illustration only and are not intended to be limiting unless otherwise specified.

Comparative Example C1

A composition was prepared employing 67.9 parts decamethylcyclopentylsiloxane, 8 parts MQ resin 804, and 24 parts of H-polymer 1,000, an Si—H-terminated organopolysiloxane crosslinker. 0.053 parts catalyst OL, a platinum catalyst available from Wacker Silicones, was added and the mixture heated at 100° for a period of three hours. At the end of this time, the product was still observed to be a liquid, with a viscosity of 265 centipoise.

Comparative Example C2

A composition was prepared in a fashion similar to Comparative Example C1, but containing 79.9 parts decamethylcyclopentasiloxane, 8 parts MQ resin 804, 12 parts H-polymer 1,000, and 0.053 parts catalyst. The product gelled into a stringy gel which was unacceptable for use in cosmetic formulations.

Comparative Example C3

A composition was prepared by diluting the gel of ex C2 to a total of 84 parts decamethylcyclopentasiloxane and 16 parts crosslinked polymer using a shear mixer. As with the case of Comparative Example C2, a stringy gel which is unsuitable for preparation of cosmetics was produced.

Comparative Example C4

The preparation of a gel was attempted employing 67.9 parts decamethylcyclopentalsiloxane, 28 parts MQ resin 804, and 4 parts EL Crosslinker 525, along with 0.053 parts platinum catalyst consisting of chloroplatinic acid in 1,2-propanediol. Rather than form a gel, a crumbly solid was produced. The amount of MQ resin and crosslinker was too high for the amount of volatile silicone oil in this case.

Comparative Example C5

An attempt was made to produce a gel using the solid of ex C4 by diluting the solid under shear to contain 84 parts decamethylcyclopentasiloxane and 16 parts crosslinked silicone. A gel was produced, however, the gel quickly separated, rendering it unsuitable for use in cosmetic products.

EXAMPLE 1

In a method similar to Comparative Example C4, a cosmetic gel was produced by employing 80 parts decamethylcyclopentasiloxane, 17.5 parts MQ resin 804, and 2.5 parts EL Crosslinker 525 with 0.53 parts platinum catalyst. A very nice gel was produced which did not separate upon standing. The gel could be homogenized with an Ultra-Turax™ mixer to produce a creamy, translucent gel of very smooth consistency, suitable for use in cosmetic products.

EXAMPLE 2

Example 1 was repeated, but employing 90 parts decamethylcyclopentasiloxane, 8.21 parts MQ resin 804, and 1.74 parts EL Crosslinker 525. After shearing the gel initially formed, a soft, creamy, translucent gel was produced.

EXAMPLE 3

Example 1 was repeated. Following cure of the composition to a gel, additional decamethylcyclopentasiloxane was added. The resulting composition thus contained, in terms of starting ingredients, 85 parts decamethylcyclopentasiloxane, 13.1 parts MQ 804 resin, and 1.87 parts EL Crosslinker 525. When sheared, a soft, creamy, transparent gel was obtained.

EXAMPLE 4

Example 1 was repeated, with half the catalyst level. A liquidy, transparent gel was obtained.

EXAMPLE 5

Example 1 was repeated employing 90 parts decamethylcyclopentasiloxane, 8.0 parts MQ resin 804, and 1.99 parts EL Crosslinker 525, and 0.0263 parts catalyst. A smooth, transparent, wet gel was obtained.

EXAMPLE 6

Example 1 was repeated, with 90 parts decamethylcyclopentasiloxane, 8.1 parts MQ resin 804, 1.87 parts EL Crosslinker 525, and 0.050 parts catalyst. After shearing, a transparent, creamy gel was obtained.

The above examples indicate that a wide variety of translucent and transparent, stable gels can be formed employing an unsaturated MQ resin and an Si—H functional crosslinker having Si—H functionality distributed along the crosslinker backbone. The comparative examples indicate that use of α,ω-Si—H functional crosslinkers leads to stringy gels, while too high a cross-linking density, regardless of the nature of the crosslinker, leads to crumbly products. It has been found that while the gels produced by the subject process are "stable", i.e. they do not separate into two or more phases nor do they solidify to "crumbly" or solid products, the gel "hardness" does increase somewhat over time. This increase in hardness is not a fatal flaw, but must be considered during manufacture if a gel with defined target characteristics is contemplated. This increase in gel hardness is thought to affect other gels produced through hydrosilylation reactions.

Applicants have discovered that the softness of hydrosilylation-type gels may be maintained over time if a minor, but effective amount of a hydrosilylation catalyst inhibitor is added to the formulation, preferably after initial gelation. When such inhibitors are used, the catalyst level must generally be increased somewhat, even though the hydrosilylation reaction has been largely completed at this point.

The catalyst inhibitors may be selected from all hydrosilylation catalyst inhibitors available. However, because the gels are intended for cosmetic formulations, some inhibitors may not be advisable for toxicological reasons, or for customer acceptance. For example, compounds such as dodecanethiol should be avoided due to its odor. However, in perfume-laden cosmetics, or where very small amounts are used, even these inhibitors may be acceptable. The amount of inhibitor generally ranges from about 0.001 to about 2 parts by weight, preferably 0.01 part to 1 part by weight based on a total gel weight of 100 parts. More preferably, 0.05 part to 0.5 part, and most preferably 0.1 part to 0.4 parts are used. The amount is preferably sufficient such that no or only very little noticeable increase in hardness occurs over a two week period of storage at room temperature. While the inhibitors are preferably added following gelation, or following the onset of gelation, the inhibitor may be added at the same time or even before catalyst addition. Additional catalyst may be required in such cases.

EXAMPLE 7

Example 1 is repeated, with 81.8 parts decamethylcyclopentasiloxane, 15.7 parts MQ resin 804, 2.24 parts E1 Crosslinker 525, and 0.100 parts catalyst. Gelling is accomplished as in previous examples, by stirring at 90°–110° for a sufficient length of time. In this example, gelation is observed after 33 minutes (ramp about 2.5° C./min.). Following this initial observation of gelation, stirring and heating are maintained for 1 hour. After this cooling water is implemented. Cooling is effected at a rate of about −1° C./min. When the material reaches 50° C., the inhibitor, 0.2 parts mercaptopropylsilsequisiloxane is added. The gel is then sheared. A creamy transluscent gel is obtained. The gel softness remains unaltered during storage for two weeks.

EXAMPLE 8

Example 7 is repeated, with 79.8 parts decamethylcyclopentasiloxane, 17.41 parts MQ resin 804, 2.49 parts E1 Crosslinker 525, and 0.100 parts catalyst. Following gelation, 0.2 parts mercaptopropylsilsequisiloxane is added with stirring. The gel is then sheared. A creamy, translucent gel whose softness does not noticeably change over two weeks storage is obtained.

By the term "creamy" with respect to gel is meant that the initial gel has been sheared to a creamy consistency. The resulting creamy gel may be pourable or relatively stiff, as the case may be. The presence of the term "creamy" distinguishes these sheared gels, which may be transparent, translucent, or opaque, from the gels immediately formed by gelation of the reactive ingredients. The terms "a" and "an" in the claims mean "one or more" unless otherwise specified.

EXAMPLE 9

In a manner similar to Example 8, a storage-stable creamy gel was prepared from 79.60 parts decamethylcyclopentasiloxane, 17.36 parts MQ resin 804, and 2.48 parts Crosslinker 525, converted to a gel with the aid of 0.523 parts hexachloroplatinic acid dissolved in 1,2-propanediol. Gelation was performed by stirring while heating to 100° C. over a period of one hour. After 38 minutes (93° C.), the mixture is seen to gel. After 1 hour, heat is removed and the product cooled to 55° C. over 40 minutes. The mixture is sheared by recycling through an IKA SD41 Super-Dispax® mixer operating at 9600 rpm and an inlet pressure of less than 10 psi for ca. 1.5 hours. The inhibitor, 0.5 parts mercaptopropylsilsesquisiloxane, is stirred into the resultant creamy gel using a propeller type mixer at 800 rpm. The product is a storage stable, smooth creamy gel which remains smooth and creamy over a period of 6 weeks.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A stable, creamy gel composition suitable for use in cosmetics, prepared by the process of
   1) gelling a mixture comprising
      a) from about 60 weight percent to about 95 percent of a low viscosity organopolysiloxane;
      b) an effective gelling amount of the hydrosilylation product of
         b)i an unsaturated organopolysiloxane resin, and
         b)ii an Si—H functional, non-resinous organopolysiloxane bearing Si—H functionality along the polysiloxane backbone;
      said hydrosilylation optionally promoted by an effective amount of a hydrosilylation catalyst,
   2) shearing said gel to form a creamy gel resistant to separation; wherein all percents are percent by weight relative to the total gel composition.

2. The creamy gel composition of claim 1, wherein said unsaturated organopolysiloxane resin is a vinyl-functional MQ resin.

3. The composition of claim 1 wherein said low viscosity organopolysiloxane comprises a linear or branched organopolysiloxane having from 2 to about 10 silicon atoms, or a cyclic organopolysiloxane having from 3 to about 6 silicon atoms.

4. The composition of claim 3 wherein the repeating siloxane moieties of said low viscosity organopolysiloxane comprise dimethylsiloxy groups.

5. The composition of claim 1 wherein said Si—H functional organopolysiloxane is a poly(methylhydrogen)(dimethyl)siloxane.

6. The composition of claim 1 wherein said low viscosity organopolysiloxane is present in an amount of 75% to 90%; said unsaturated organopolysiloxane is present in an amount of about 5% to about 25%, and said Si—H functional crosslinker is present in an amount of about 1–8%.

7. The composition of claim 1 wherein said low viscosity organopolysiloxane is present in an amount of 80% to 90%; said unsaturated organopolysiloxane is present in an amount of about 10% to about 20%, and said Si—H functional crosslinker is present in an amount of about 1–5%.

8. The composition of claim 1, wherein prior to shearing, additional low viscosity organopolysiloxane is added.

9. The composition of claim 1, further comprising an amount of hydrosilylation catalyst inhibitor effective to decrease changes in said creamy gel softness upon storage as compared to a similar gel prepared without said inhibitor.

10. The composition of claim 9, wherein said inhibitor is a mercaptoalkyl-functional siloxane.

11. The composition of claim 10, wherein said inhibitor is a mercaptoalkyl-functional silsesquisiloxane or mercaptoalkyl-fuctionalized low viscosity polyorganosiloxane oil.

12. A process for the preparation of a creamy gel suitable for cosmetic applications, said process comprising:
   a) providing a composition comprising
      a)i a low viscosity organopolysiloxane
      a)ii an unsaturated organopolysiloxane resin
      a)iii an Si—H functional organopolysiloxane bearing Si—H functionality along the polysiloxane backbone;
   b) hydrosilylating a)ii with a)iii to form a gel;
   c) shearing said gel to form a creamy gel.

13. The process of claim 12, further comprising
   a)iv an effective hydrosilylating promoting amount of a hydrosilylation catalyst.

14. The process of claim 13 further comprising adding an amount of a hydrosilylation catalyst inhibitor effective to decrease change in softness of said creamy gel upon storage as compared to a similar gel prepared without said inhibitor.

15. The process of claim 14 wherein said inhibitor is added during or following step b).

16. A cosmetic preparation comprising the creamy gel of claim 1 and cosmetically acceptable ingredients.

17. The cosmetic preparation of claim 16, wherein said preparation is one selected from antiperspirants, deodorants, sun care, after sun care, moisturizers, face creams, hand creams, skin lotions, facial powder, eye shadow, liquid foundation, liquid-to-powder foundations, lipsticks, hair conditioners, and volume enhancers.

18. A process for decreasing the change in softness of creamy organopolysiloxane gels containing in excess of 60 weight percent low viscosity organopolysiloxane and a gelation composition prepared by hydrosilylating an unsaturated hydrocarbon or unsaturated hydrocarbon-functional organopolysiloxane with an Si—H functional organopolysiloxane in the presence of a hydrosilylation catalyst, said process comprising adding an amount of a hydrosilylation catalyst inhibitor effective to decrease change in softness of said creamy gel upon storage as compared to a similar gel prepared without said inhibitor.

19. The process of claim 18, wherein said hydrosilylation catalyst inhibitor is an organic sulfur compound.

20. The process of claim 18, wherein said inhibitor comprises a mercaptoalkyl-functional organopolysiloxane.

21. The process of claim 18, wherein said inhibitor comprises a mercaptopropyl silsesquisiloxane.

* * * * *